United States Patent
Guzman

(10) Patent No.: US 11,529,497 B1
(45) Date of Patent: Dec. 20, 2022

(54) CENTERING DEVICE FOR A CATHETER

(71) Applicant: ORLANDO HEALTH, INC., Orlando, FL (US)

(72) Inventor: Edgar D. Guzman, Orlando, FL (US)

(73) Assignee: Orlando Health, Inc., Orlando, FL (US)

( * ) Notice: Subject to any disclaimer, the term of this patent is extended or adjusted under 35 U.S.C. 154(b) by 0 days.

(21) Appl. No.: 17/693,068

(22) Filed: Mar. 11, 2022

Related U.S. Application Data

(63) Continuation of application No. 17/574,797, filed on Jan. 13, 2022.

(51) Int. Cl.
*A61M 25/04* (2006.01)
*A61M 25/00* (2006.01)
*A61M 25/10* (2013.01)

(52) U.S. Cl.
CPC ........ *A61M 25/04* (2013.01); *A61M 25/0043* (2013.01); *A61M 25/0071* (2013.01); *A61M 25/0074* (2013.01); *A61M 2025/0096* (2013.01); *A61M 2025/1047* (2013.01)

(58) Field of Classification Search
CPC .......... A61M 25/0074; A61M 25/0071; A61M 2025/0096; A61M 2025/1047
See application file for complete search history.

(56) References Cited

U.S. PATENT DOCUMENTS

| | | | |
|---|---|---|---|
| 1,828,986 A | 10/1931 | Stevens | |
| 1,972,428 A | 9/1934 | Richard | |
| 2,541,691 A | 2/1951 | Eicher | |
| 5,275,610 A | 1/1994 | Eberbach | |
| 5,509,900 A | 4/1996 | Kirkman | |
| 5,730,726 A | 3/1998 | Klingenstein | |
| 5,769,821 A | 6/1998 | Abrahamson et al. | |
| 5,795,322 A | 8/1998 | Boudewijn | |
| 5,810,874 A | 9/1998 | Lefebvre | |
| 5,954,742 A | 9/1999 | Osypka | |
| 5,954,745 A | 9/1999 | Gertler et al. | |
| 5,976,172 A * | 11/1999 | Homsma | A61F 2/01 606/191 |
| 6,071,263 A | 6/2000 | Kirkman | |
| 6,159,139 A | 12/2000 | Chiu | |
| 6,558,349 B1 | 5/2003 | Kirkman | |
| 6,558,406 B2 | 5/2003 | Okada | |
| 7,713,216 B2 | 5/2010 | Dubey et al. | |
| 7,938,799 B2 | 5/2011 | Epstein et al. | |
| 8,052,659 B2 | 11/2011 | Ravenscroft et al. | |
| 8,070,761 B2 | 12/2011 | Weber et al. | |
| 8,152,786 B2 | 4/2012 | Shapland et al. | |
| 8,568,355 B2 | 10/2013 | Min et al. | |
| 8,696,623 B2 | 4/2014 | Sellers | |
| 8,708,986 B2 | 4/2014 | Shapland et al. | |

(Continued)

*Primary Examiner* — Bradley J Osinski
(74) *Attorney, Agent, or Firm* — Crowell & Moring LLP

(57) ABSTRACT

A catheter may include an elongated tube enclosing at least one catheter lumen, and a centering device coupled to a distal end of the elongated tube, wherein the centering device includes a plurality of legs. Each leg of the plurality of legs may include a first end fixed to an outer surface of the elongated tube. Each leg of the plurality of legs may include an outward bias such that a central portion of each leg of the plurality of legs is spaced radially outward from the elongated tube when the centering device is in an expanded state.

19 Claims, 7 Drawing Sheets

(56) References Cited

U.S. PATENT DOCUMENTS

| | | |
|---|---|---|
| 8,728,106 B2 | 5/2014 | Weber et al. |
| 8,840,601 B2 | 9/2014 | Salahieh et al. |
| 9,358,037 B2 | 6/2016 | Farhangnia et al. |
| 9,451,984 B2 | 9/2016 | Zhou et al. |
| 9,511,206 B2 | 12/2016 | Hofius et al. |
| 9,561,080 B2 | 2/2017 | Lamoureux et al. |
| 9,597,108 B2 * | 3/2017 | Ahn .................... A61B 17/221 |
| 9,980,840 B2 | 5/2018 | Havel et al. |
| 10,117,659 B2 | 11/2018 | Zhou et al. |
| 10,569,066 B2 | 2/2020 | Hayakawa et al. |
| 10,932,932 B2 | 3/2021 | Havel et al. |
| 2001/0025187 A1 | 9/2001 | Okada |
| 2004/0204738 A1 | 10/2004 | Weber et al. |
| 2006/0253099 A1 | 11/2006 | Noone |
| 2007/0232981 A1 | 10/2007 | Ravenscroft et al. |
| 2007/0239197 A1 | 10/2007 | Dubey et al. |
| 2008/0039786 A1 | 2/2008 | Epstein et al. |
| 2008/0108960 A1 | 5/2008 | Shapland et al. |
| 2010/0082004 A1 | 4/2010 | Shapland et al. |
| 2011/0257622 A1 | 10/2011 | Salahieh et al. |
| 2012/0035635 A1 | 2/2012 | Weber et al. |
| 2012/0143139 A1 | 6/2012 | Min et al. |
| 2013/0030461 A1 | 1/2013 | Marks et al. |
| 2013/0123708 A1 | 5/2013 | Sellers |
| 2014/0200603 A1 | 7/2014 | Zhou et al. |
| 2014/0257092 A1 | 9/2014 | Lamoureux et al. |
| 2014/0277008 A1 | 9/2014 | Farhangnia et al. |
| 2015/0265299 A1 | 9/2015 | Cooper et al. |
| 2015/0306350 A1 | 10/2015 | Hofius et al. |
| 2016/0066936 A1 | 3/2016 | Weber et al. |
| 2016/0095602 A1 | 4/2016 | Hayakawa et al. |
| 2016/0120566 A9 | 5/2016 | Farhangnia et al. |
| 2016/0158045 A1 | 6/2016 | Havel et al. |
| 2016/0361076 A1 | 12/2016 | Zhou et al. |
| 2018/0235792 A1 | 8/2018 | Havel et al. |
| 2019/0046236 A1 | 2/2019 | Kassab et al. |

* cited by examiner

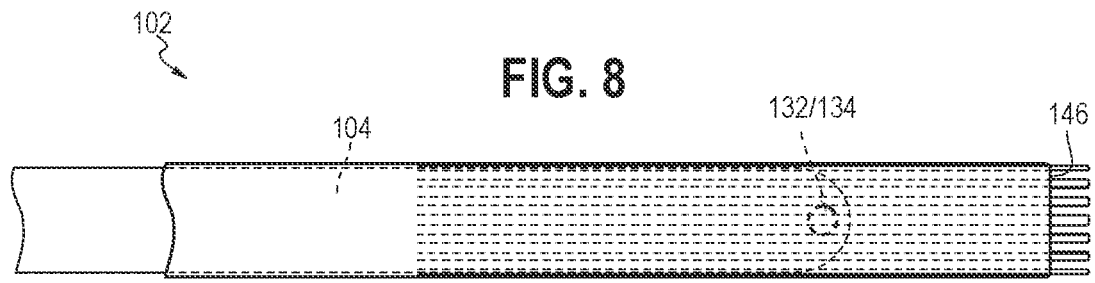
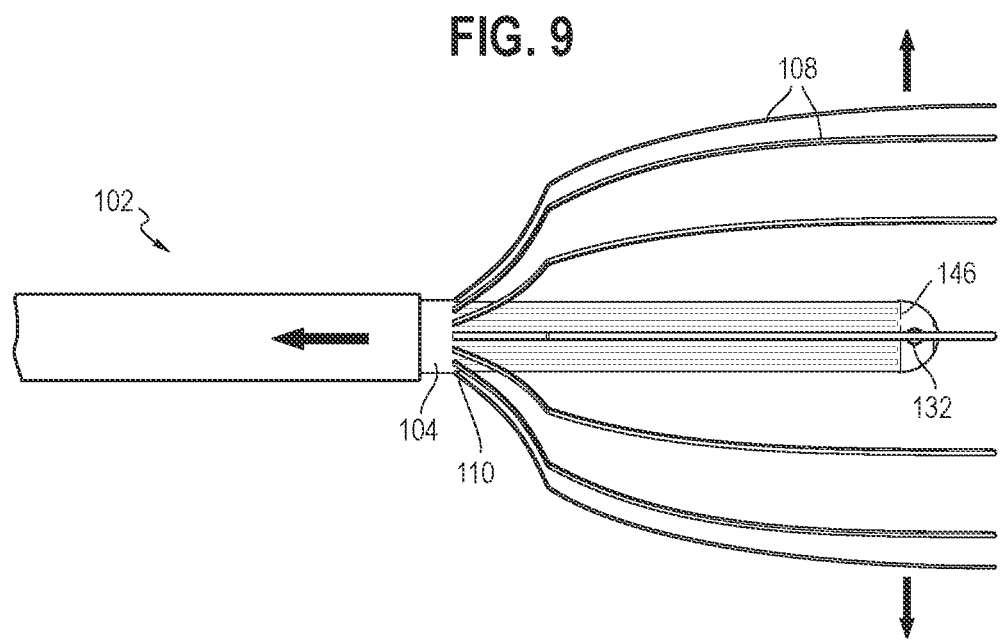

CENTERING DEVICE FOR A CATHETER

RELATED APPLICATION

This application is a continuation of U.S. patent application Ser. No. 17/574,797, titled "CENTERING DEVICE FOR A CATHETER," filed Jan. 13, 2022, which is hereby incorporated by reference in its entirety.

TECHNICAL FIELD

The present disclosure is generally related to a centering device for a catheter. More particularly, the present disclosure describes a device secured to a distal end of a vascular catheter that prevents an elongated tube's distal end from contacting a vessel wall.

BACKGROUND

Catheters medical devices that are often used to administer or collect fluids located within interior spaces of a patient body. For example, a catheter may be used in a vascular space for administering a medication and/or collecting blood, sometimes simultaneously. One particular application of a catheter is hemodialysis, where blood is removed from a vessel, cleaned with a dialyzer, and then re-administered through a separate port/opening. While such procedures have been used with success, vascular catheters utilizing suction often misbehave, as they tend to lean against vessel walls. The vessel walls may block or otherwise prevent access to the ports/openings leading to the catheter lumen. The embodiments described in this document address this issue.

BRIEF DESCRIPTION OF THE DRAWINGS

The embodiments discussed herein may be better understood with reference to the following drawings and description. The components in the figures are not necessarily to scale. Moreover, in the figures, like-referenced numerals designate corresponding parts throughout the different views.

FIG. 8 is an illustration showing an additional embodiment of a catheter where a set of legs of a centering device extend distally beyond an elongated tube of the catheter in accordance with certain aspects of the present disclosure.

FIG. 9 is an illustration showing the catheter of FIG. 8 in an expanded, deployed state in accordance with certain aspects of the present disclosure.

FIG. 10 shows the catheter in a delivery state and where FIG. 11 shows the catheter in an expanded deployed state in accordance with certain aspects of the present disclosure.

DETAILED DESCRIPTION

Figure 1:
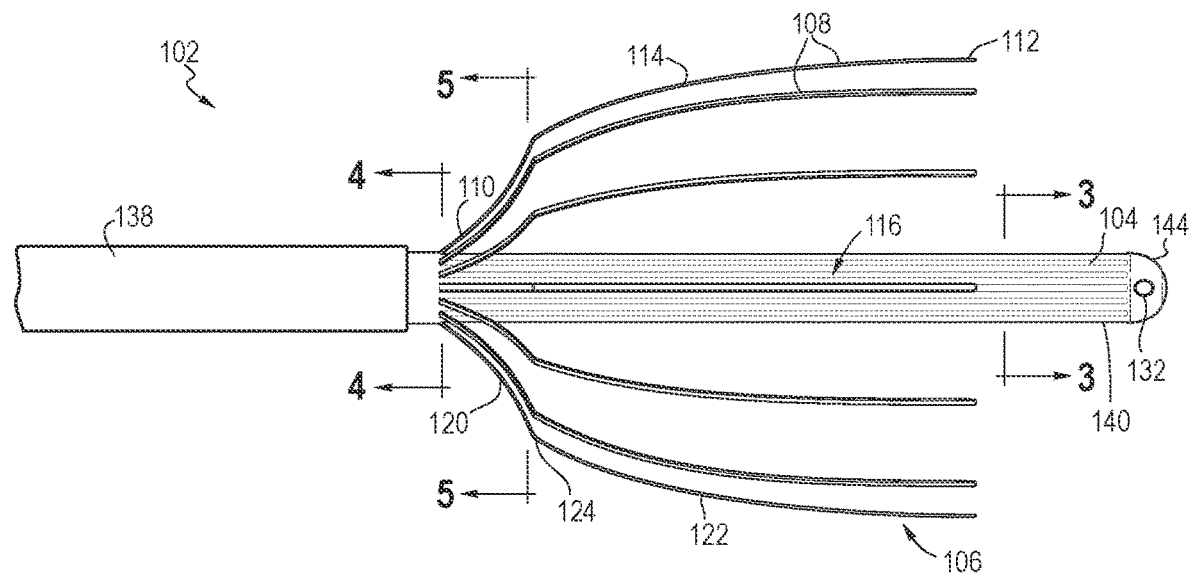
FIG. 1 is an illustration showing a side view of a catheter having a centering device in an expanded state in accordance with certain aspects of the present disclosure.

Various aspects are described below with reference to the drawings in which like elements generally are identified by like numerals. The relationship and functioning of the various elements of the aspects may be better understood by reference to the following detailed description. However, aspects are not limited to those illustrated in the drawings or explicitly described below. It also should be understood that the drawings are not necessarily to scale, and in certain instances details may have been omitted that are not necessary for an understanding of aspects disclosed herein, such as conventional fabrication and assembly.

The terms "distal" and "proximal" are used herein in the common usage sense where they refer respectively to a tool/patient-end of a device or related object and the opposite end (e.g., typically the handle/doctor-end of the device or related object).

As discussed in the background above, existing vascular catheters, particularly when utilizing suction, may become blocked if the lumen opening is obstructed by a vessel wall. The embodiments herein provide a catheter 102 that addresses this issue. In particular, as shown in FIGS. 1-7, the catheter 102 includes an elongated tube 104, which may have at least one lumen therein (as discussed in more detail below). At least partially surrounding the elongated tube is a centering device 106. In exemplary embodiments, the centering device 106 is located at or near the distal end 140 of the elongated tube 104. Generally, the centering device 106 is advantageous for preventing the distal end of the elongated tube, and particularly openings 132, 134 (leading to one or more lumens), from approaching and contacting a vessel wall.

Figure 2:
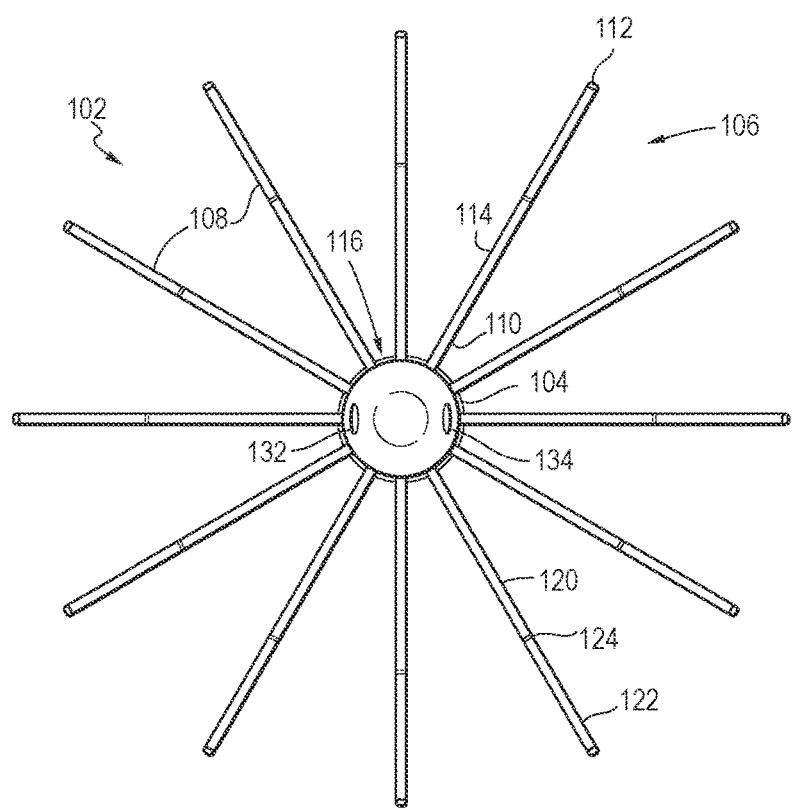
FIG. 2 is an illustration showing a front view of the catheter having the expanded centering device from FIG. 1.

FIGS. 1-2 depict the centering device 106 in an expanded state, which may be the state typically assumed when the catheter 102 is placed within a vessel and a medical procedure is underway. As shown, the centering device 106 may include a plurality of legs 108 that generally fan radially outward from an outer surface 116 of the elongated tube 104. While each leg 108 may be substantially the same in structure and function (as shown), it is contemplated that certain legs may differ from others, which may be advantageous where different legs are intended to provide different, direction-oriented spacing. Each leg 108 may include a first end 110 fixed to an outer surface 116 of the elongated tube 104 and a second end 112 that is spaced radially away/outward from the outer surface 116. For example, in certain applications, and when fully expanded, the legs 108 may open to form a cavity having a diameter of between about 20 mm and about 25 mm, which matches the diameter of the superior vena cava in a human patient. The outer diameter of the elongated tube 104 may be significantly less, e.g., about 4 mm in certain embodiments (e.g., at least 50% less than the diameter of the expanded legs, and perhaps 75% (or more) less). To assume and retain this configuration, the legs 108 may be formed of a flexible and resilient material that has an outward bias or spring-like tendency. Without limitation, carbothane may be used, which is a form of polyurethane.

Each of the legs 108 may also include a central portion 114 that extends from the first end 110 to the second end 112. The central portions 114 may be elongated strips of material that form the primary structure of the legs 108. In certain embodiments, the central portions 114 may be specifically shaped such that the central portion 114 has a particular outer dimension and/or outer profile shape for engaging the inner wall of a body lumen. For example, in the depicted embodiment, the central portions 114 of the legs 108 include an optional concave profile portion 120 adjacent to the first ends 110, which may be advantageous for ensuring the central portion 114 quickly reaches a sufficiently large diameter as it extends distally. The legs 108 may also include a set of optional convex profile portions 122 extending from the concave profile portions 120 to the second ends 112, which may be advantageous for providing smoothness to the outer profile to prevent snagging, cutting, etc. of body tissue engaging the legs 108. A crimp 124 or other junction structure may be located between each concave profile portion 120 and convex profile portion 122. In other embodiments, the legs 108 may have a different shape and/or orientation for providing a different profile shape of the centering device 106.

Figure 6:
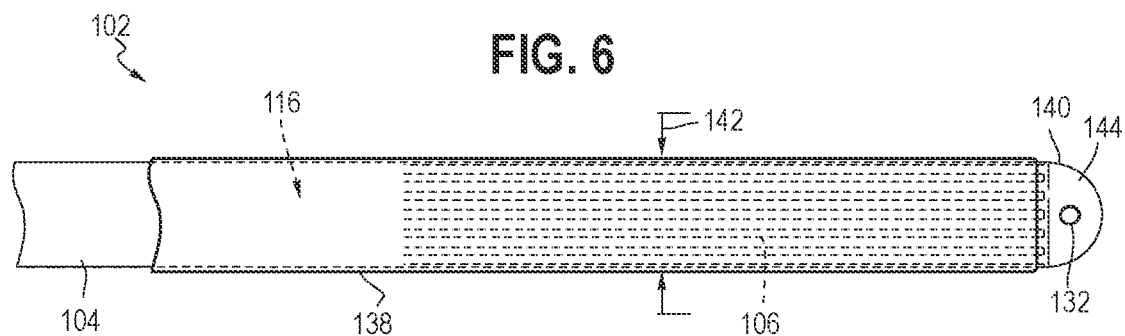
FIG. 6 is an illustration showing a side view of a catheter similar to the catheter from FIG. 1, wherein the centering device is in a collapsed delivery state in accordance with certain aspects of the present disclosure.

The legs 108 of the centering device 106 may be formed with any suitable structure or method. In one non-limiting exemplary example, the legs 108 may be formed by displacing a portion of the outer surface 116 of the elongated tube 104 (e.g., via slicing or peeling) but leaving the displaced material attached at an end. In other words, referring to FIG. 7A, the legs 108 may be cut from the outer surface 116 of the elongated tube 104 itself. After formation, the legs 108 may correspond with a set of depressions or channels beneath each leg 108. This method of formation and resulting structure is advantageous for several reasons. First, the resulting structure results in the legs 108 being integral with the elongated tube, meaning that the material of the outer surface 116 and the legs 108 is uniform, and no separate attachment means is needed. Thus, the leg 108 may be secured without the use of an adhesive or other attachment mechanism, thereby enhancing the durability of the leg 108 to reduce the risk of disengagement within a patient's body while also reducing manufacturing cost relative to other embodiments. Second, since each leg 108 may have a corresponding depression 126 sized substantially the same as its respective leg 108, the outer profile of the centering device 106 may be substantially compact, uniform, and consistent with the tube's outer surface 116 when the legs 108 are in the retracted/collapsed, delivery state. For example, as shown in FIG. 6, the outer-facing surface of the elongated tube 104 and legs 108 may snugly fit and generally match the inner-facing surface of the sheath 138.

In some implementations, the second ends 112 of the legs 108 may have a blunted shape or another suitable shape such that they do not cut or otherwise cause injury to body tissue upon contact. For example, the second ends 112 may be rounded/curved, chamfered, tapered, conical, slope, smoothed, or otherwise structured without sharp edges that may come into contact with body tissue. Advantageously, a medical professional may move the device within the patient, including distally and proximally, without undue concern over causing injury. Notably, when the legs 108 are formed via material displacement from the elongated tube 104 (as discussed below), blunting of the second ends 112 of the legs may be accomplished after general leg formation. It is further contemplated that other edges of the legs 108 (and/or other components) may be smoothed/blunted to remove sharp edges and burrs during the manufacturing process.

The elongated tube 104 may include a more than one lumen, such as a first lumen 128 and a second lumen 130 divided by a barrier. In certain embodiments (e.g., those where one lumen is used for injection and another for suction, as discussed below), the first lumen 128 may be fluidly isolated from the second lumen 130 within the elongated tube 104, such as by using a bifurcating barrier 136 or another suitable structure. The first opening 132 may be configured to provide access to the first lumen 128, and the second opening 134 may be configured to provide access to the second lumen 130. More or fewer than two lumens may be included, and each lumen may be associated with more than one opening in other embodiments.

Figure 3:
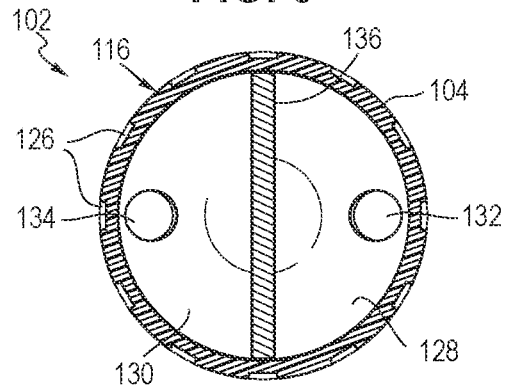
FIG. 3 is an illustration showing a section view about section 3-3 of FIG. 1.
Figure 4:
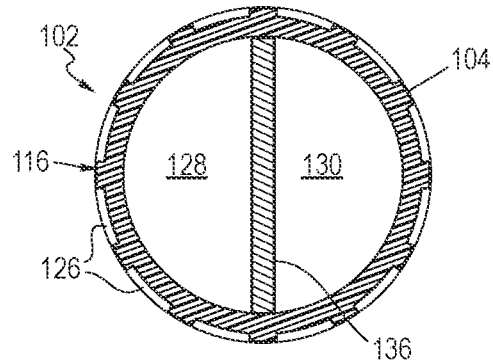
FIG. 4 is an illustration showing a section view about section 4-4 of FIG. 1.
Figure 5:
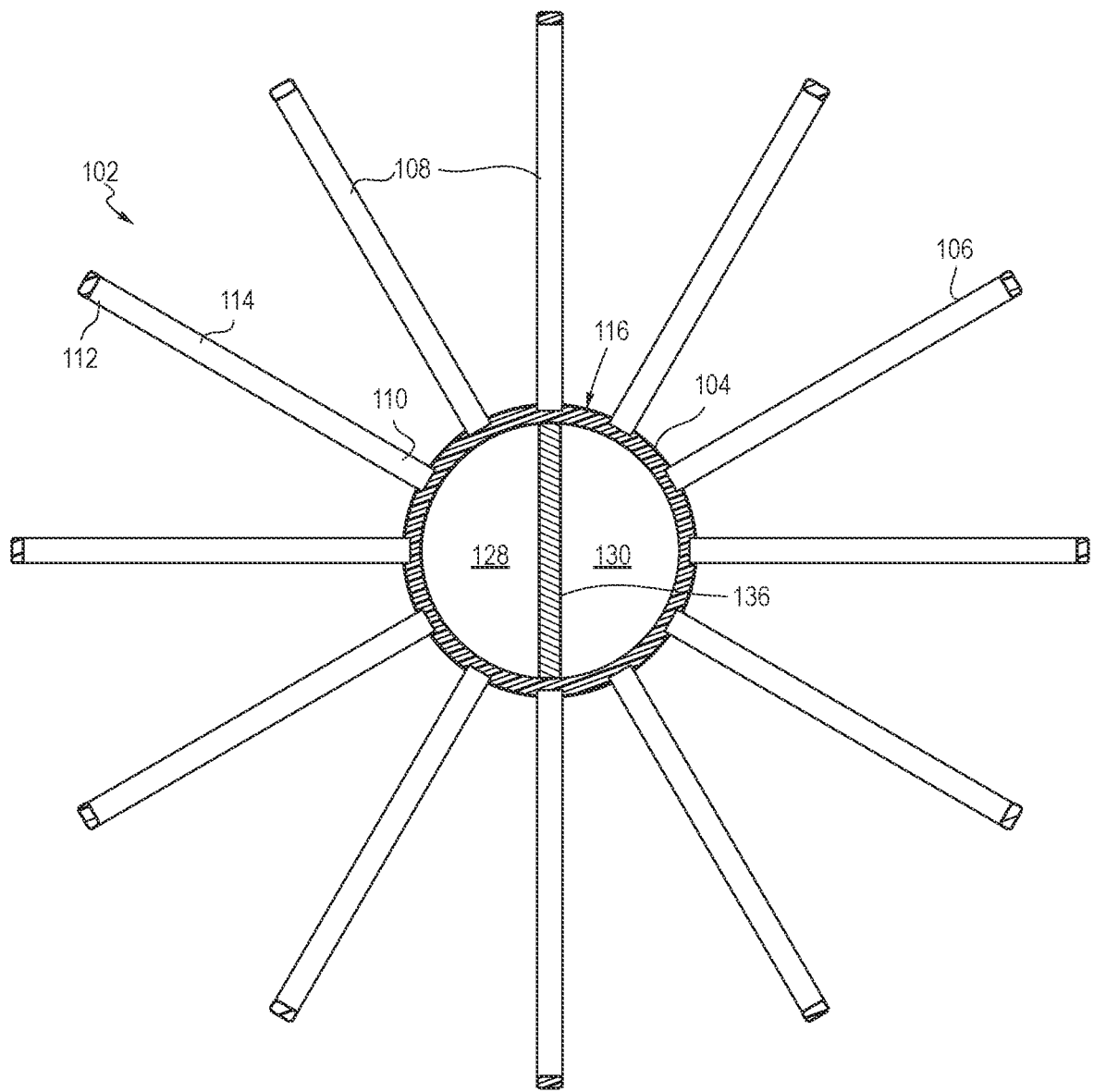
FIG. 5 is an illustration showing a section view about section 5-5 of FIG. 1.

The first opening 132 and/or the second opening 134 may face opposite one another (e.g., as best shown in FIG. 3). Advantageously, this orientation may prevent or reduce the likelihood of a phenomenon known as recirculation, which occurs when blood that has just been dialyzed and re-inserted into the vessel immediately re-enters the inflow opening.

Figure 7:
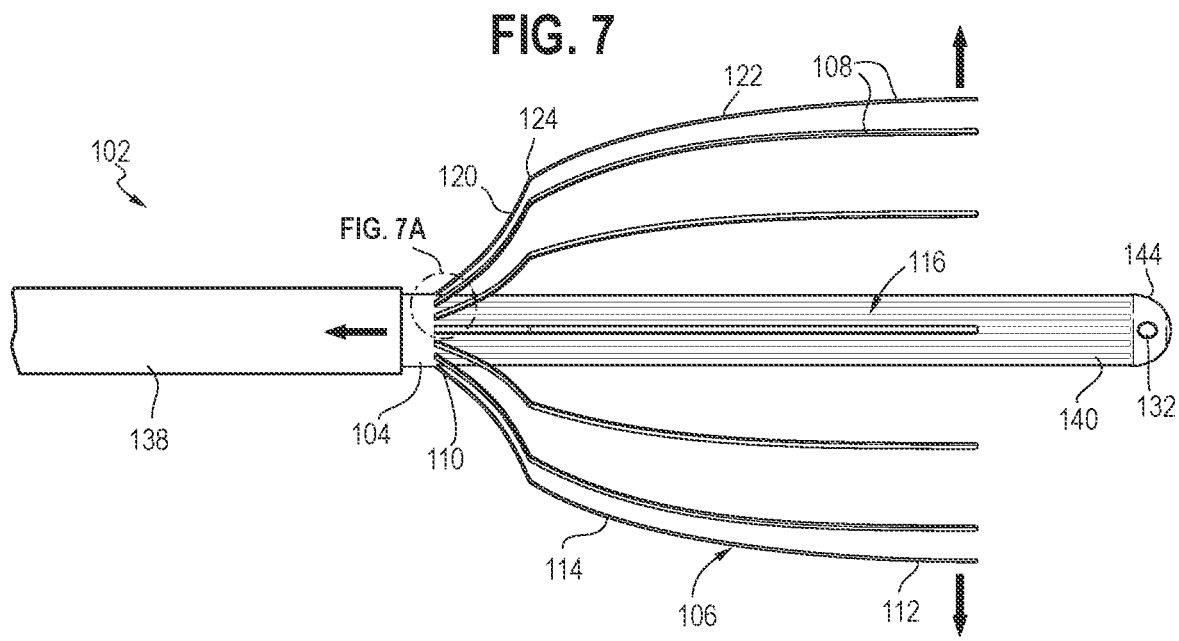
FIG. 7 is an illustration showing a side view of the catheter from FIG. 6, where a sheath has moved proximally to release a set of centering device legs in accordance with certain aspects of the present disclosure.
Figure 7A:
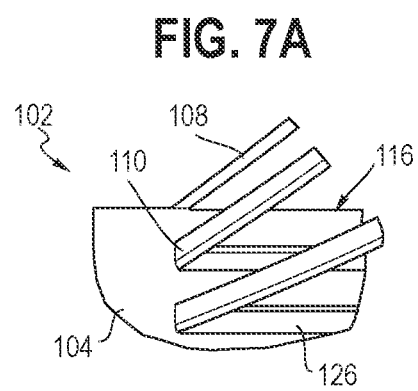
FIG. 7A is an illustration showing an enlarged view of portion 7A identified in FIG. 7.

FIGS. 6-7 show the catheter 102 when in the compact delivery state and the expanded deployed state, respectively. As shown in FIG. 6, a sheath 138 is placed at least partially over the legs 108 and prevents outward movement of the legs 108 such that they remain adjacent to the elongated tube 104. The overall outer diameter of the device is much smaller when the sheath restricts the legs 108, and in this embodiment is equal to an outer diameter 142 of the sheath 138. Advantageously, the device may be placed into and moved through a patient body when in this configuration, allowing the device to quickly and easily reach a target location while fitting through tight spaces, rounding turns, etc. When the distal end 140 of the device is properly located, the sheath 138 may be slide proximally relative to the centering device 106 such that it may selectively uncover the legs 108. In summary, when the legs 108 are covered (FIG. 6), they may be prevented from fanning outward, but when the sheath 138 slides proximally into its position of FIG. 7, the internal bias of the legs 108 may cause the centering device 106 to assume its expanded state without further manipulation from the sheath 138. In other embodiments, the sheath 138 may peel away or otherwise be removed, for example. Notably, the legs 108 have sufficient flexibility such that they can be removed from the body without needed to be re-engaged by the sheath 138 without concern over damaging the body, which is advantageous in certain embodiments for limiting the need for control wires or other features that extend from the sheath 138 to a handle of the device.

As shown in FIG. 6, when in the compact delivery state, the legs 108 may terminate adjacent to an endcap 144 or other distal end portion of the catheter 102. This structure may be the result of the legs 108 being formed from displaced material of the elongated tube, where the cutting/peeling process (as mentioned above) begins near the terminus of the elongated tube 104 to substantially maximize the length of the legs 108. One extended radially outward as shown in FIG. 7, the second ends 112 of the legs may retract distally due to their fanning outward. Thus, once in the expanded state, the second ends 112 of the legs 108 may be located proximally relative to the distal end 140 of the elongated tube 104. At least one of the openings 132, 134 may therefore be located distally relative to the second ends 112 of the legs 108 such that the legs 108 are not radially coextensive with the openings 132, 134. Notably, the openings 132, 134 extend through the endcap 144 in the depicted embodiment, but this is not necessarily the case. In alternative implementations, the openings 132, 134 may extend through the sidewalls of the elongated tube 104. When the endcap 144 is included, it may alternatively lack any openings, and in some embodiments it may include a curved, tapered, or otherwise blunt surface for ease of movement of the elongated tube through the body during deployment.

FIGS. 8-9 show an alternative arrangement. As shown, the legs 108 extend further distally relative to the distal terminus 146 of the elongated tube 104. In this embodiment, the legs 108 are radially coextensive with the openings 132, 134 and also the distal terminus of the elongated tube 104. Advantageously, the protection of the openings 132, 134 by the legs 108 may be enhanced since the openings 132, 134 are within a "cage" structure formed by the legs 108. To form this embodiment, the portion of the elongated tube that extends beyond the first ends 110 of the legs 108 may be shortened (e.g., via cutting), for example.

Figure 10:
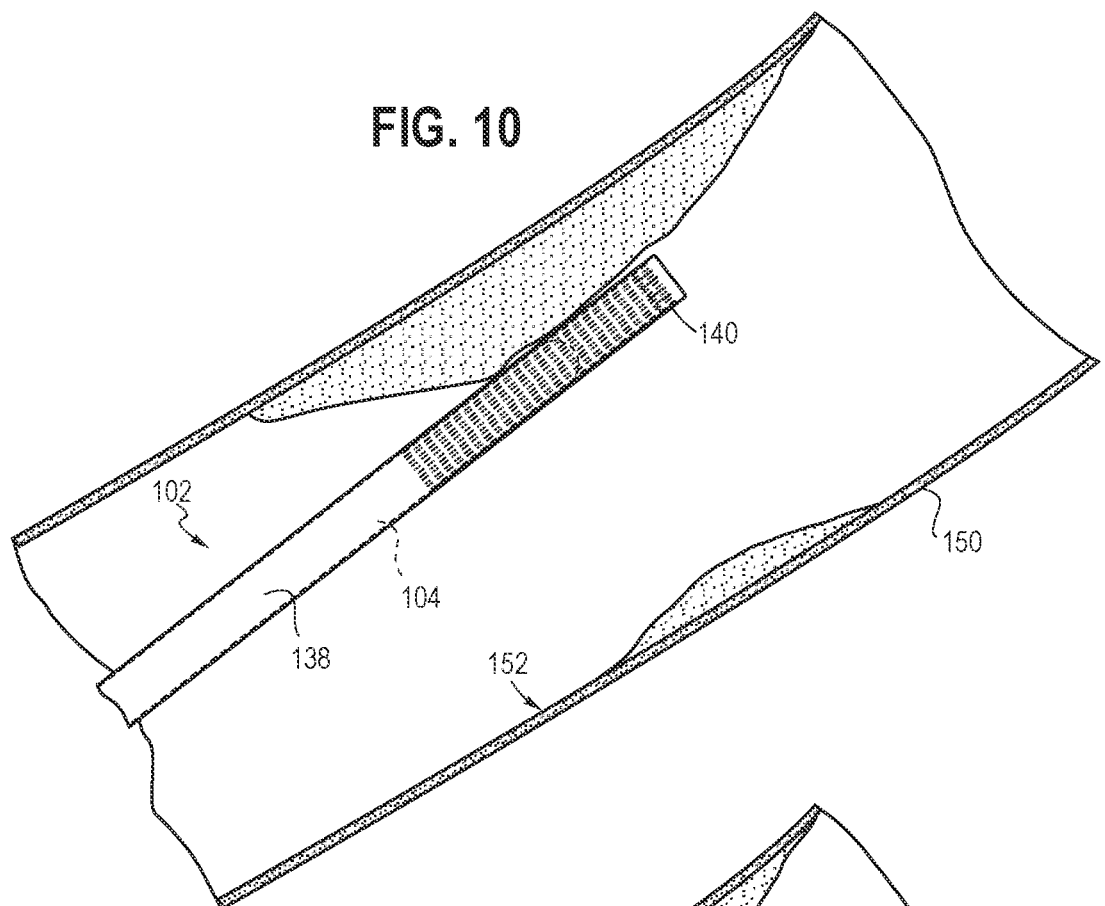
FIGS. 10 and 11 are illustrations showing the catheter from FIG. 8 during operation within a body vessel, where
Figure 11:
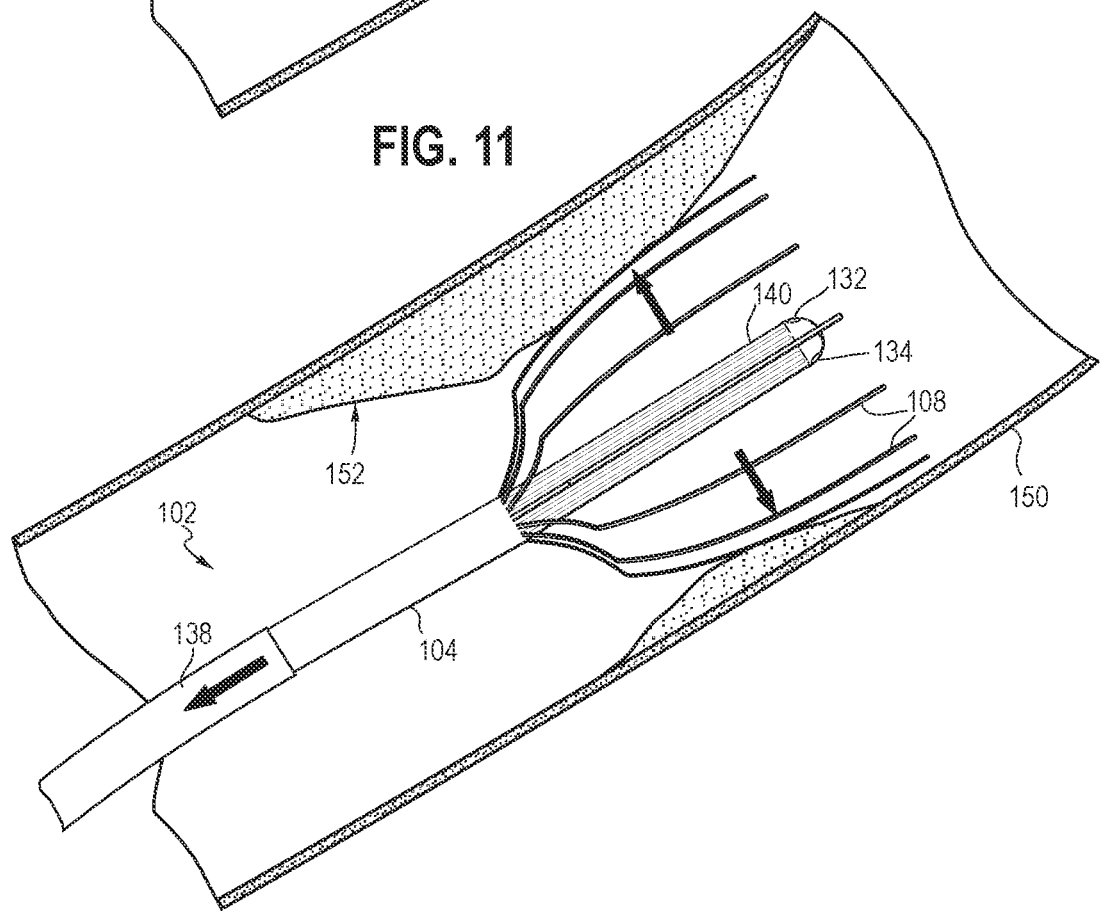

FIGS. 10-11 show an illustration of the catheter 102 from FIGS. 8-9 when inserted into a patient body. As shown in FIG. 10, the distal end of the device may be placed into the body and moved into an appropriate position, such as within a patient's vessel. When ready, the physician or other medical professional may retract the sheath 138 such that the legs 108 are released and fan outward. When required based on the sizing of the body lumen 150, the legs 108 may contact and press against the outer wall(s) 152 of the body lumen 150, thereby ensuring the distal end 140 of the elongated tube 104 (and particularly the openings 132, 134) remain spaced from the walls 152. Flexibility of the legs 108 may provide softness/cushioning such that the legs 108 retain space between the openings and the vessel walls without damaging the vessel walls.

Figure 12:
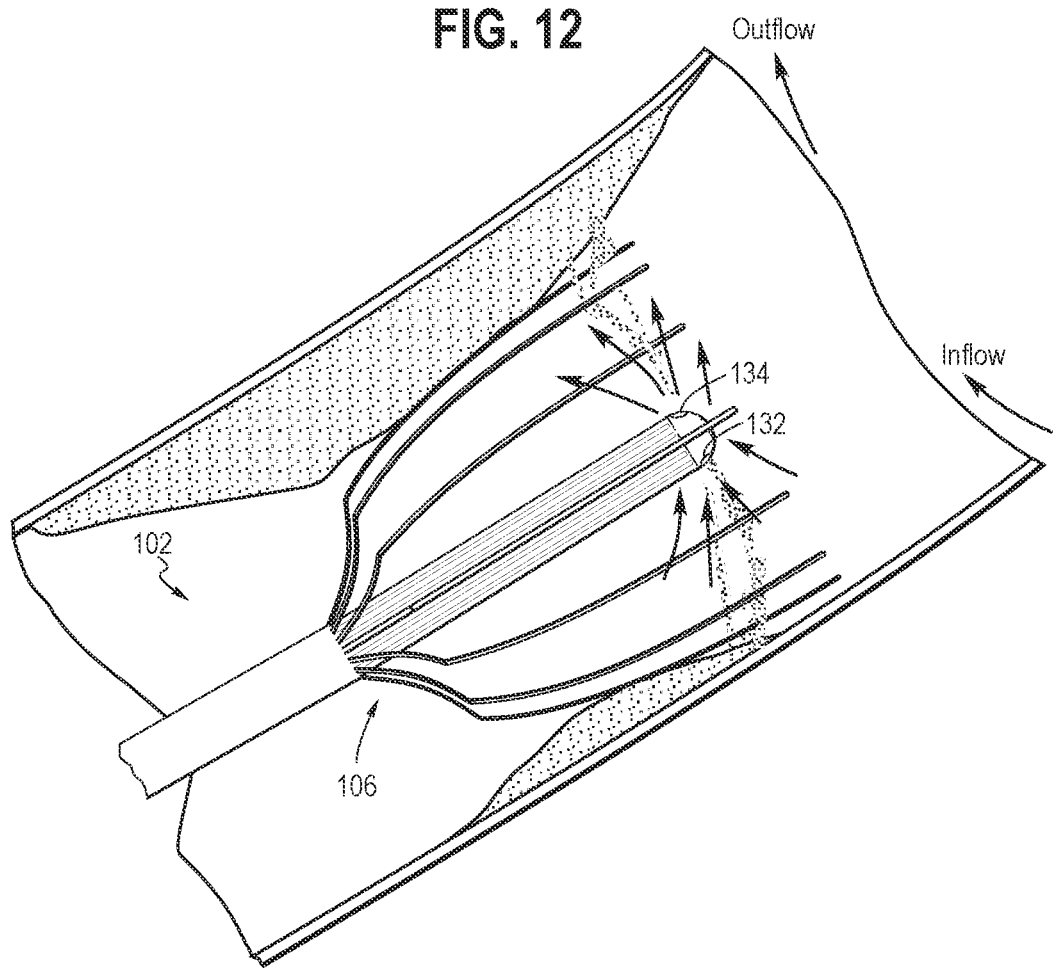
FIG. 12 is an illustration showing the catheter of FIGS. 8-11 during a medical procedure involving suction and administration of a fluid in accordance with certain aspects of the present disclosure.

FIG. 12 shows the catheter 102 during a medical procedure, such as during hemodialysis. Other procedures are alternatively contemplated. In this particular procedure, the first opening 132 may lead to a first opening that is exposed to a vacuum, which results in blood inflow. After dialysis, this same blood may be re-introduced through the second opening 134. Since the first opening 132 and the second opening 134 face opposite directions, unwanted hemodialysis recirculation may be very unlikely, particularly since the openings remain free from obstructions due to operation of the centering device 106. This embodiment has advantageous over embodiments requiring openings to be located at the catheter tip, for example, since such embodiments may lack the ability for side openings due to vessel wall obstructions discussed above.

Figure 13:
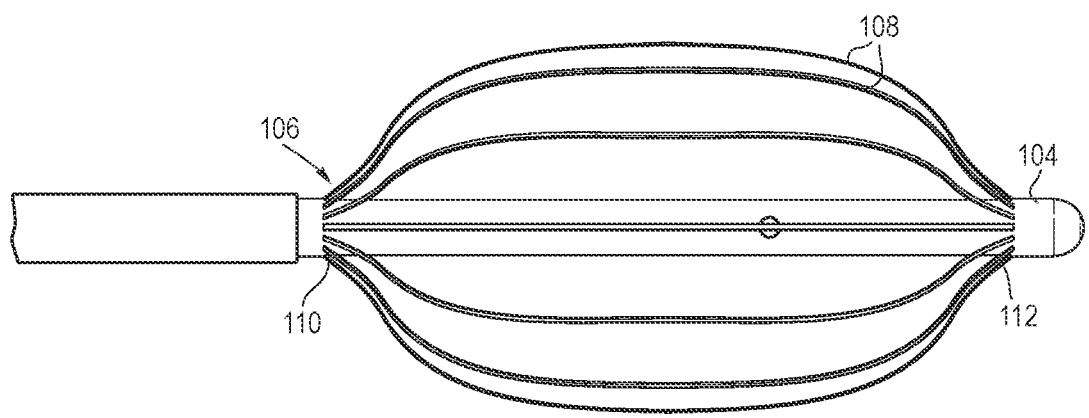
FIG. 13 is an illustration showing an additional embodiment of a catheter with a centering device, the centering device having legs with two ends attached to the underlying elongated tube in accordance with certain aspects of the present disclosure.

FIG. 13 shows an alternative embodiment of a centering device 106. The primary difference between this embodiment and those above is that the second ends 112 of the legs 108 are secured to the elongated tube 104, thereby providing two points of attachment between the legs 108 and the elongated tube 104. This embodiment may be advantageous where enhanced stability of the legs 108 is required, where the legs 108 provide support for another device (e.g., a balloon or other inflation device), etc. To form this embodiment, at least end of the legs 108 may be secured via a separate securement structure, such as with the use of an adhesive, a mechanical clamp or fastener, a tie, or the like. Alternatively, it is contemplated that the legs 108 may be stretched or otherwise elongated along their longitudinal axes such that they are capable of buckling outward relative to the underlying elongated tube 104. Notably, the opening 132 may be located proximally of the second ends 112, but other locations are also contemplated.

Figure 14:
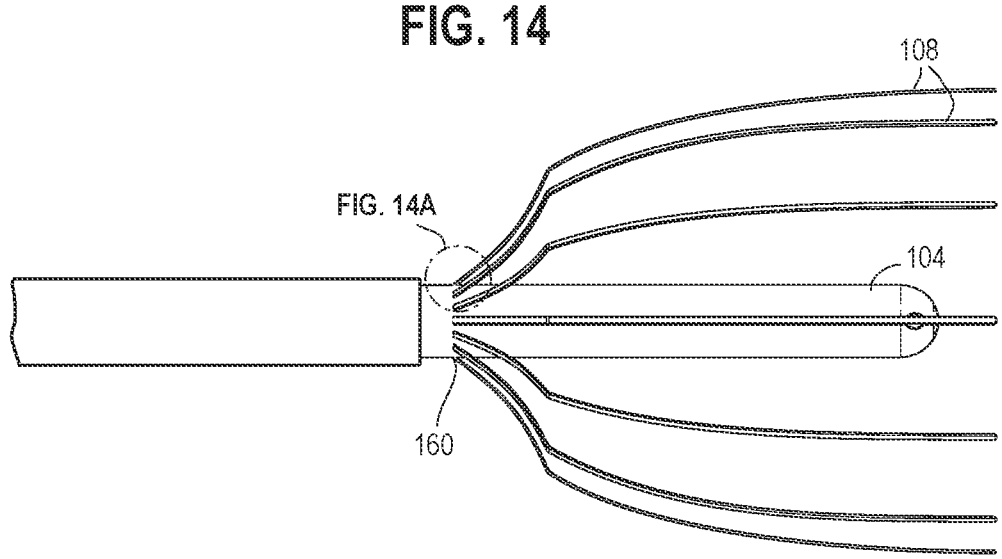
FIG. 14 is an illustration showing an additional embodiment of a catheter with a centering device, the centering device having legs that are formed from a material different than a material of the underlying elongated tube in accordance with certain aspects of the present disclosure
Figure 14A:
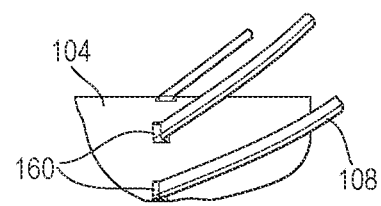
FIG. 14A is an illustration showing an enlarged view about 14A identified in FIG. 14.

FIGS. 14 and 14A show another alternative embodiment, which is similar to the embodiment of FIG. 9 but with one primary exception: the legs 108 are not integral with the elongated tube 104, but are instead attached to the elongated tube 104 in another way at a junction 160. For example, the legs 108 may be secured to the elongated tube with an adhesive, a mechanical clamp or fastener, a tie, or the like. While the prior embodiments may be advantageous in certain circumstances, the present embodiment may be advantageous where a particular material is desirable for the legs 108 that is not easily accommodated by the elongated tube (or vice versa). For example, in certain embodiments, the elongated tube 104 may be formed of a polymer material while the legs 108 may be formed of a shape memory metal (e.g., Nitinol), which may enhance the ability for precise operation of the legs 108 when in a patient body.

While various embodiments have been described, it will be apparent to those of ordinary skill in the art that many more embodiments and implementations are possible. Accordingly, the embodiments described herein are examples, not the only possible embodiments and implementations.

Having described various aspects of the subject matter above, additional disclosure is provided below that may be consistent with the claims originally filed with this disclosure. In describing this additional subject matter, reference may be made to the previously described figures. Any of the following aspects may be combined, where compatible.

A $1^{st}$ aspect includes a catheter. The catheter may include an elongated tube enclosing at least one catheter lumen, and a centering device coupled to a distal end of the elongated tube, wherein the centering device includes a plurality of legs. Each leg of the plurality of legs may include a first end fixed to an outer surface of the elongated tube. Each leg of the plurality of legs may include an outward bias such that a central portion of each leg of the plurality of legs is spaced radially outward from the elongated tube when the centering device is in an expanded state.

In a $2^{nd}$ aspect, the catheter of aspect 1 may be implemented such that each leg of the plurality of legs includes a second end located distally of the first end, wherein the central portion extends from the first end to the second end, and wherein the second end is spaced radially outward from the elongated tube when the centering device is in the expanded state.

In a 3rd aspect, the catheter of aspect 2 may be implemented such that at least one leg of the plurality of legs includes a concave profile portion and a convex profile portion, the concave profile portion extending distally from the first end, and the convex profile portion extending proximally from the second end.

In a 4th aspect, the catheter of aspect 2 may be implemented such that the second end of each leg of the plurality of legs includes a blunt outer surface.

In a 5th aspect, the catheter of aspect 1 may be implemented such that the legs of the plurality of legs are integral with the outer surface of the elongated tube such that a material forming the outer surface is uniform with the material forming the legs.

In a 6th aspect, the catheter of aspect 1 may be implemented such that the elongated tube includes a first opening configured to provide access to a first catheter lumen, wherein the first opening is located distally of terminal distal end of at least one leg of the plurality of legs when the centering device is in the expanded state.

In a 7th aspect, the catheter of aspect 1 may be implemented such that the elongated tube includes a first opening configured to provide access to a first catheter lumen, wherein the first opening is at least partially surrounded by the legs of the centering device such that the legs are configured to prevent engagement between the first opening and a target body surface.

In an 8th aspect, the catheter of aspect 1 may be implemented such that the elongated tube includes a first opening configured to provide access to a first catheter lumen, wherein the elongated tube includes a second opening configured to provide access to a second catheter lumen, and wherein the first catheter lumen is fluidly isolated from the second catheter lumen within the elongated tube.

In a 9th aspect, the catheter of aspect 8 may be implemented such that the first opening extends through a wall of the elongated tube and faces a first direction, wherein the second opening extends through a wall of the elongated tube and faces a second direction, and wherein the first direction is substantially opposite the second direction.

In a 10th aspect, the catheter of aspect 1 may include a sheath configured for preventing outward movement of the legs of the centering device when the centering device is in a delivery state.

In an 11th aspect, the catheter of aspect 1 may include an endcap forming a distal terminus of the elongated tube, wherein the endcap lacks an opening to an inner lumen within the catheter.

In a 12th aspect, the catheter of aspect 1 may be implemented such that the elongated tube includes a plurality of depressions corresponding to the plurality of legs such that the legs are received by the depressions when the centering device is in the delivery state.

A 13th aspect includes a catheter. The catheter may include an elongated tube enclosing at least one catheter lumen; a first opening located at a distal end of the elongated tube, the first opening being configured to provide access to a first lumen, the first lumen extending through the elongated tube; a second opening located at the distal end of the elongated tube, the second opening being configured to provide access to a second lumen, the second lumen extending through the elongated tube and being fluidly isolated relative to the first lumen within the elongated tube; and a centering device coupled to the distal end of the elongated tube, wherein the centering device is moveable between a delivery state and an expanded state, and wherein the centering device includes a bias towards the expanded state.

In a 14th aspect, the catheter of aspect 13 may be implemented such that the centering device includes a plurality of legs, wherein each leg of the plurality of legs includes a distal end that is spaced radially outward from the elongated tube when the centering device is in the expanded state.

In a 15th aspect, the catheter of aspect 14 may be implemented such that the distal end of each leg of the plurality of legs includes a blunt outer surface.

In a 16th aspect, the catheter of aspect 14 may be implemented such that the legs of the plurality of legs are integral with an outer surface of the elongated tube such that a material forming the outer surface is uniform with the material forming the legs.

In a 17th aspect, the catheter of aspect 13 may include an endcap forming a distal terminus of the elongated tube, wherein the endcap lacks an opening to an inner lumen within the catheter.

An 18th aspect includes a method. The method may include forming a catheter having an elongated tube and a centering device, wherein the centering device is coupled to a distal end of the elongated tube, wherein the centering device includes a plurality of legs, wherein each leg of the plurality of legs includes a first end fixed to an outer surface of the elongated tube, and wherein each leg of the plurality of legs includes an outward bias such that a central portion of each leg of the plurality of legs is spaced radially outward from the elongated tube when the centering device is in an expanded state.

In a 19th aspect, the method of aspect 18 may be implemented such that forming the legs includes displacing a portion of the outer surface of the elongated tube, and wherein a central portion of each of the legs consists of the displaced portion of the outer surface of the elongated tube.

In a 20th aspect, the method of aspect 19 may include attaching the legs to the outer surface of the elongated tube after forming the elongated tube and after forming the legs of the centering device.

I claim:

1. A catheter, comprising:
    an elongated tube enclosing at least one catheter lumen and having a distal terminus; and
    a centering device coupled to a distal end of the elongated tube, wherein the centering device includes a plurality of legs,
    wherein each leg of the plurality of legs includes a first end fixed to an outer surface of the elongated tube,
    wherein each leg of the plurality of legs includes an outward bias such that a central portion of each leg of the plurality of legs is spaced radially outward from the elongated tube when the centering device is in an expanded state, and
    wherein at least one leg of the plurality of legs extends distally beyond the distal terminus, and
    wherein the elongated tube includes a first opening configured to provide access to a first catheter lumen, wherein the first opening is at least partially surrounded by the legs of the centering device such that the legs are configured to prevent engagement between the first opening and a target body surface.

2. The catheter of claim 1, wherein each leg of the plurality of legs includes a second end located distally of the first end, wherein the central portion extends from the first end to the second end, and wherein the second end is spaced radially outward from the elongated tube when the centering device is in the expanded state.

3. The catheter of claim 2, wherein at least one leg of the plurality of legs includes a concave profile portion and a convex profile portion, the concave profile portion extending distally from the first end, and the convex profile portion extending proximally from the second end.

4. The catheter of claim 2, wherein the second end of each leg of the plurality of legs includes a blunt outer surface.

5. The catheter of claim 1, wherein the legs of the plurality of legs are integral with the outer surface of the elongated tube such that a material forming the outer surface is uniform with the material forming the legs.

6. The catheter of claim 1, wherein the elongated tube includes a first opening configured to provide access to a first catheter lumen, wherein the first opening is located distally of terminal distal end of at least one leg of the plurality of legs when the centering device is in the expanded state.

7. The catheter of claim 1, wherein the elongated tube includes a second opening configured to provide access to a second catheter lumen, and wherein the first catheter lumen is fluidly isolated from the second catheter lumen within the elongated tube.

8. The catheter of claim 7, wherein the first opening extends through a wall of the elongated tube and faces a first direction, wherein the second opening extends through the wall of the elongated tube and faces a second direction, and wherein the first direction is substantially opposite the second direction.

9. The catheter of claim 1, further comprising a sheath configured for preventing outward movement of the legs of the centering device when the centering device is in a delivery state.

10. The catheter of claim 1, further comprising an endcap forming a distal terminus of the elongated tube, wherein the endcap lacks an opening to an inner lumen within the catheter.

11. The catheter of claim 1, wherein the elongated tube includes a plurality of depressions corresponding to the plurality of legs such that the legs are received by the depressions when the centering device is in a delivery state.

12. A catheter, comprising:
an elongated tube enclosing at least one catheter lumen;
a first opening located at a distal end of the elongated tube, the first opening being configured to provide access to a first lumen, the first lumen extending through the elongated tube;
a second opening located at the distal end of the elongated tube, the second opening being configured to provide access to a second lumen, the second lumen extending through the elongated tube and being fluidly isolated relative to the first lumen within the elongated tube; and
a centering device coupled to the distal end of the elongated tube, wherein the centering device is moveable between a delivery state and an expanded state, and wherein the centering device includes a bias towards the expanded state, and
wherein the centering device includes a plurality of legs, wherein each leg of the plurality of legs includes a distal end that is spaced radially outward from the elongated tube when the centering device is in the expanded state, and wherein each end lacks a direct connection to the elongated tube when the centering device is in the delivery state.

13. The catheter of claim 12, wherein the distal end of each leg of the plurality of legs includes a blunt outer surface.

14. The catheter of claim 12, wherein the legs of the plurality of legs are integral with an outer surface of the elongated tube such that a material forming the outer surface is uniform with the material forming the legs.

15. The catheter of claim 12, further comprising an endcap forming a distal terminus of the elongated tube, wherein the endcap lacks an opening to an inner lumen within the catheter.

16. A catheter, comprising:
an elongated tube enclosing at least one catheter lumen and having a distal terminus; and
a centering device coupled to a distal end of the elongated tube, wherein the centering device includes a plurality of legs,
wherein each leg of the plurality of legs includes a first end fixed to an outer surface of the elongated tube,
wherein each leg of the plurality of legs includes an outward bias such that a central portion of each leg of the plurality of legs is spaced radially outward from the elongated tube when the centering device is in an expanded state, and
wherein the distal terminus is at least partially surrounded by the legs of the centering device such that the legs are configured to prevent engagement between the distal terminus and a target body surface.

17. The catheter of claim 16, wherein each leg of the plurality of legs includes a second end located distally of the first end, wherein the central portion extends from the first end to the second end, and wherein the second end is spaced radially outward from the elongated tube when the centering device is in the expanded state.

18. The catheter of claim 17, wherein the second end of each leg of the plurality of legs includes a blunt outer surface.

19. The catheter of claim 16, wherein the elongated tube includes a first opening configured to provide access to a first catheter lumen, wherein the elongated tube includes a second opening configured to provide access to a second catheter lumen, and wherein the first catheter lumen is fluidly isolated from the second catheter lumen within the elongated tube.

* * * * *